United States Patent
Vandewalle

(10) Patent No.: US 7,141,054 B2
(45) Date of Patent: Nov. 28, 2006

(54) METHOD AND APPARATUS FOR INTRAMEDULLARY DELIVERY OF A MATERIAL

(75) Inventor: Mark Victor Vandewalle, Pierceton, IN (US)

(73) Assignee: Biomet, Inc., Warsaw, IN (US)

( * ) Notice: Subject to any disclaimer, the term of this patent is extended or adjusted under 35 U.S.C. 154(b) by 390 days.

(21) Appl. No.: 10/357,189

(22) Filed: Feb. 3, 2003

(65) Prior Publication Data

US 2004/0153090 A1 Aug. 5, 2004

(51) Int. Cl.
*A61B 17/58* (2006.01)
*A61F 2/00* (2006.01)

(52) U.S. Cl. .................................................... 606/92
(58) Field of Classification Search .............. 606/53, 606/86, 92, 93, 94
See application file for complete search history.

(56) References Cited

U.S. PATENT DOCUMENTS

| | | | |
|---|---|---|---|
| 3,724,076 A | 4/1973 | Schmitz | |
| 3,741,204 A | 6/1973 | Thiele | |
| 4,419,095 A * | 12/1983 | Nebergall et al. | 604/103.1 |
| 4,466,435 A | 8/1984 | Murray | |
| 4,627,434 A * | 12/1986 | Murray | 606/63 |
| 4,653,487 A | 3/1987 | Maale | |
| 5,116,377 A * | 5/1992 | Skripitz et al. | 623/23.19 |
| 5,340,362 A * | 8/1994 | Carbone | 623/23.19 |
| 5,403,318 A * | 4/1995 | Boehringer et al. | 606/82 |
| 5,717,030 A * | 2/1998 | Dunn et al. | 523/111 |
| 5,800,439 A | 9/1998 | Clyburn | |
| 5,871,484 A | 2/1999 | Spievack et al. | |
| 6,048,346 A | 4/2000 | Reiley et al. | |
| 6,261,586 B1 * | 7/2001 | McKay | 424/423 |
| 6,371,985 B1 * | 4/2002 | Goldberg | 623/16.11 |
| 6,387,098 B1 | 5/2002 | Cole et al. | |
| 6,579,533 B1 * | 6/2003 | Tormala et al. | 424/426 |
| 6,582,439 B1 * | 6/2003 | Sproul | 606/92 |
| 6,610,079 B1 * | 8/2003 | Li et al. | 606/232 |
| 6,632,235 B1 * | 10/2003 | Weikel et al. | 606/192 |
| 6,679,886 B1 * | 1/2004 | Weikel et al. | 606/79 |
| 6,832,988 B1 * | 12/2004 | Sproul | 600/459 |
| 6,990,368 B1 * | 1/2006 | Simon et al. | 600/425 |
| 2002/0082605 A1 | 6/2002 | Scribner et al. | |

FOREIGN PATENT DOCUMENTS

DE     100 42 423 A     3/2002

OTHER PUBLICATIONS

Partial European Search Report for Application No. EP 04 25 0572 dated May 18, 2004.

* cited by examiner

*Primary Examiner*—Eduardo C. Robert
*Assistant Examiner*—Anu Ramana
(74) *Attorney, Agent, or Firm*—Harness, Dickey & Pierce, P.L.C.

(57) ABSTRACT

A method and apparatus to apply a selected material to the intramedullary canal of a selected bone. The apparatus generally includes a reservoir area from which the selected material can be expressed. The apparatus further includes an outlet or nozzle which allows for directing of the material as it is being expressed from the reservoir. Further, the apparatus allows the material to be expressed into the intramedullary canal during a procedure involving the intramedullary canal. The apparatus obviates forming an additional incision to apply the material.

17 Claims, 2 Drawing Sheets

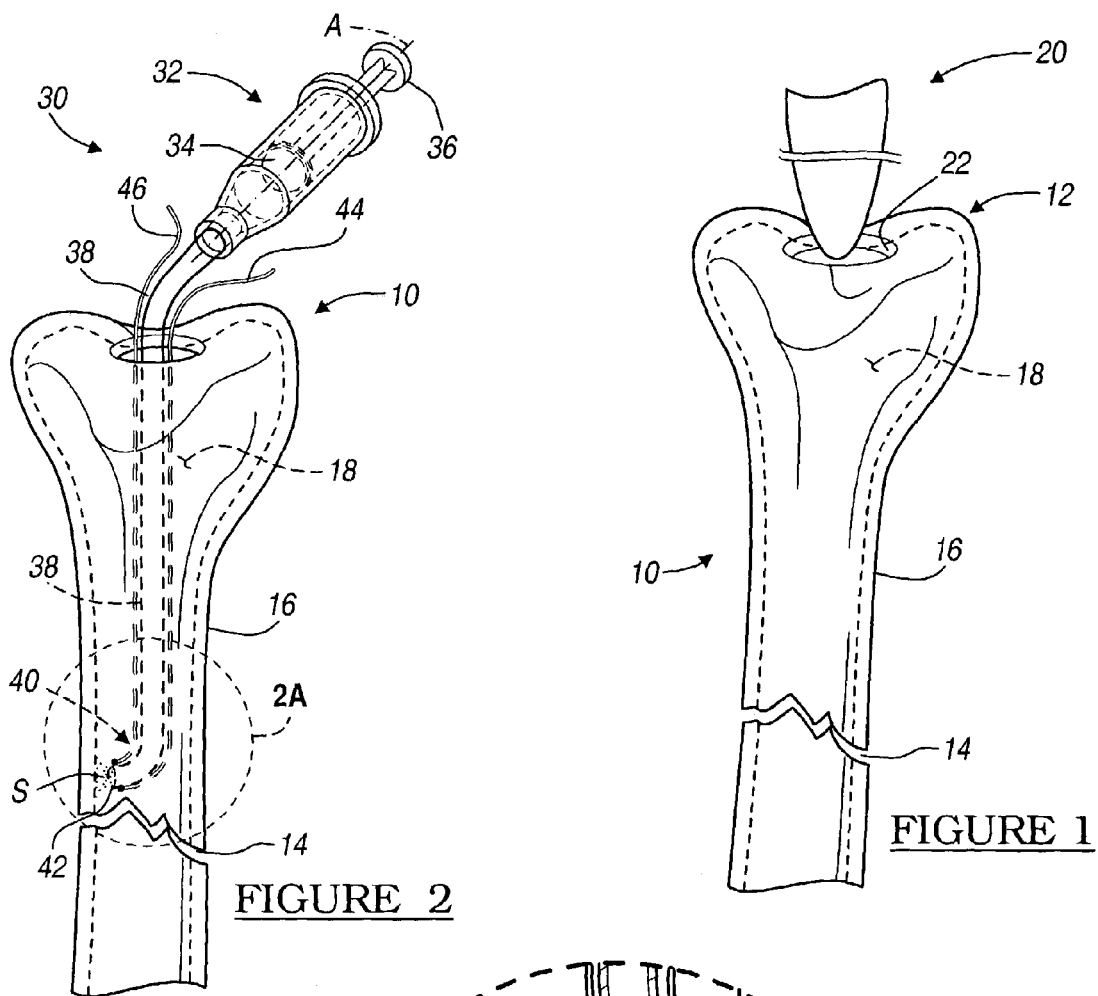
FIGURE 1
FIGURE 2
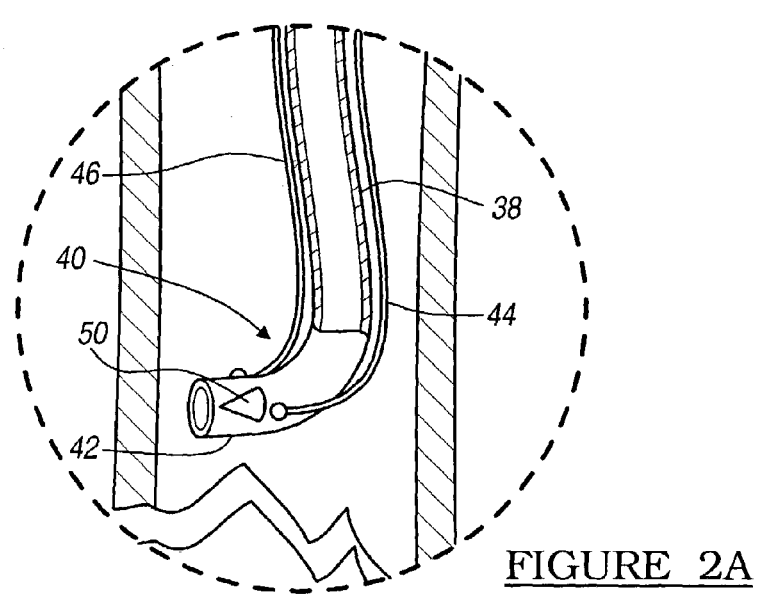
FIGURE 2A

METHOD AND APPARATUS FOR INTRAMEDULLARY DELIVERY OF A MATERIAL

FIELD

The present invention relates to a method and apparatus for applying a material, and more particularly, to a method and apparatus for applying the material to an intramedullary canal of a bone during a surgical procedure.

BACKGROUND

Various biological materials can assist in healing of various traumatic injuries. Specifically various autologous materials of human blood can be used as an autograph to assist in healing of a particular injury. For example, platelets may be placed on a bone fracture to assist and increase the healing rate of the bone fracture. In addition, platelets may be placed on a soft tissue to assist in healing of that wound.

Platelets may be placed on an injury either in the harvested concentration or in a more concentrated manner. Therefore, platelets may be concentrated from a blood sample and placed onto the selected area to increase healing of the selected area. Generally, it is desired to place the platelet concentrate near or adjacent to the injury that is desired to be healed.

Because the platelet concentrate is used to increase healing of an injury that has already occurred, it is desired to reduce additional trauma to apply the platelet concentrate. Therefore, it is desirous to provide the platelet concentrate to a pre-existing injury or surgical incision rather than producing an auxiliary opening to apply the platelet concentrate. It is also desirable to direct the platelet concentrate to a selected area which may not be uniformly distributed within a particular region. It is also desirable to apply a specific or selected amount of material to a selected area depending upon the injury and concentration of the platelet concentrate.

SUMMARY

A method and apparatus to provide a platelet concentrate into the intramedullary area of a bone is provided. During the procedure, it may be necessary to place an intramedullary (IM) nail within a long bone. For example, a fracture of the femur may be repaired by placing IM nail through the IM canal to strengthen the femur bone. An application of platelet concentrate may be supplied through the IM canal to assist in healing of the fracture and the canal itself after the surgery. Therefore, the intramedullary canal may be prepared to receive the nail. After the platelet concentrate is applied, the IM nail may be placed in the IM canal. The apparatus may be used to direct the platelet concentrate to a selected area within the canal which may be adjacent to an existing fracture or within the canal itself. It will be understood that the application of that material may be to any selected bone such as the humerus and tibia.

According to an embodiment an apparatus for applying a material to a selected area within a bone is described. The apparatus comprises a reservoir extending along a first axis to selectively contain the material. An expressing member is provided to selectively express the material from the reservoir. Also, a nozzle directs the material, as the material is expressed from the reservoir, at an angle relative to the first axis. The reservoir is adapted to be disposed within the bone while the material is expressed.

According to various other embodiments an applicator is able to apply a bio-material into a bone prior to the implantation of a selected implant. The applicator comprises a body defining a reservoir and extending along a first axis. A nozzle is operably associated with the body such that the nozzle directs the material in a selected direction at an angle to the first axis. A piston is movable within the body to express material from the body and through the nozzle. The nozzle is adapted to be disposed within a section of the bone. Also, the nozzle is detectable with an external viewing device to allow for a selection of the selected direction for expressing the material.

According to alternative embodiments a method is described for applying a material to a selected area of an interior of a bone with an applicator that has a nozzle to direct the flow of material from the applicator. The method comprises opening a portal to the interior of the bone such that a selected portion of the interior of the bone is exposed. The applicator is positioned in the selected interior portion of the bone. After positioning the applicator material is expressed from the applicator.

An additional alternative embodiment includes a method of applying a bio-active material to a selected interior of a bone of an anatomy before implanting an implant. The method comprises selecting a bone appropriate for implantation of the implant and selecting the implant for the selected bone. A portion of the intramedullary canal is displaced from the selected bone, appropriate for implantation of the selected implant. An applicator is positioned within the bone in the portion of the intramedullary canal displaced for implantation of the implant. The bio-active material is then expressed into the intramedullary canal. Also the selected implant is implanted in the intramedullary canal.

Further areas of applicability will become apparent from the detailed description provided hereinafter. It should be understood that the detailed description and various examples, while indicating the various embodiments are intended for purposes of illustration only and are not intended to limit the scope of the following claims.

BRIEF DESCRIPTION OF THE DRAWINGS

The present description will become more fully understood from the detailed description and the accompanying drawings, wherein:

FIG. 1 is a partial cross-sectional view of a femur prepared to receive an intramedullary nail;

FIG. 2 is a partial cross-sectional view of a femur and an applicator according to a first embodiment;

FIG. 2A is a detailed view of the outlet of the applicator according to the embodiments illustrated in FIG. 2;

DETAILED DESCRIPTION OF VARIOUS EMBODIMENTS

Figure 3:
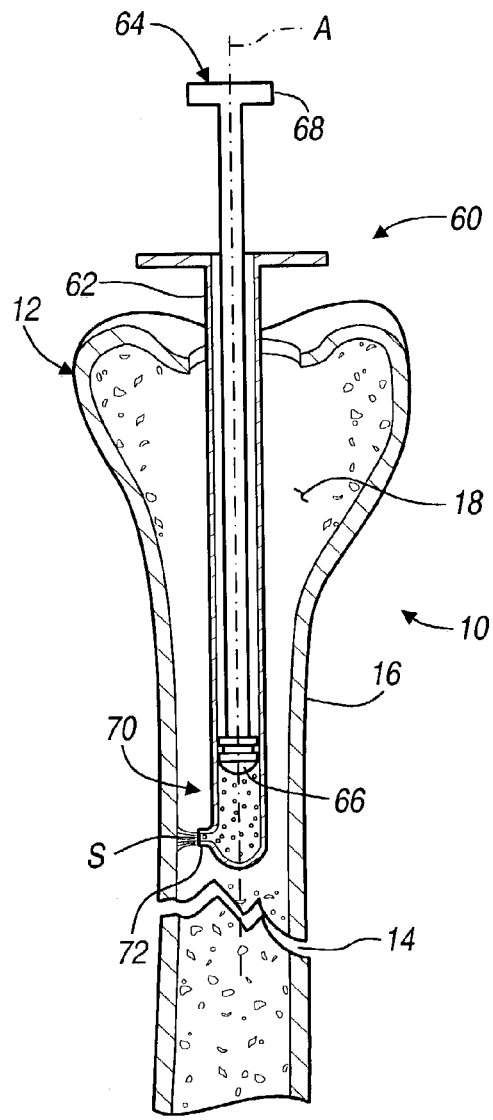
FIG. 3 is a partial cross-sectional view of the femur including an applicator according to a second embodiment.

The following description of various embodiments is merely exemplary in nature and is in no way intended to limit the description, the claims and its application or uses. Moreover, although the following description and illustrations refer specifically to applying a platelet concentrate to the intramedullary canal of a femur it would be understood that the platelet concentrate may be applied to any bone. For example, the platelet concentrate may also be applied to the IM canal of the humurus or the tibia. Therefore, it will be understood that the present description and claims is applicable to any appropriate bone in the body.

With reference to FIG. 1, a femur 10 that includes a distal end 12, which may operably articulate with the tibia to form the knee joint, is illustrated. During an activity or because of degradation of the bone, a fracture or break 14 may occur in the femur 10. The femur 10 generally includes a cancelous and a cortical bony portion 16 which surrounds an intramedullary canal 18. It would be understood that the proportions illustrated in the figures are merely exemplary and meant to clarify the following discussion and are not meant to be anatomically correct or to exact scale. Nevertheless, the fracture 14 may extend through the cancellous and cortical hard bone 16 and through the intramedulary canal 18. When the fracture 14 occurs, and especially when the bone structure of the femur 10 is weakened due to disease or injury, an IM nail 20 may be positioned within the femur 10 to reinforce the structure of the femur 10 after implantation of the IM nail 20.

Methods to implant the IM nail 20 into the intramedullary canal 18 of the femur 10, are generally known, therefore, only a cursory discussion below will be provided. A portal or opening resection 22 is formed in an appropriate portion of the femur 10, such as the distal end 22. After the opening 22 is formed the IM nail 20 may be positioned through the opening 22. Therefore, the IM nail 20 displaces a portion of the naturally remaining material in the IM canal 18 to allow for implantation of the IM nail 20.

Alternatively, after the opening 22 is formed a selected portion of the intramedullary canal 18 may be reamed or removed. The selected volume of the intramedullary canal 18 may be removed in any generally known method, such as reaming, scraping, drilling, using a rasp, or any other appropriate method. Nevertheless, the intramedullary canal 18 may be cleared of a selected portion or volume of material appropriate to receive the IM nail 20. Specifically, the IM nail 20 fits snugly within the IM canal 18, but not so snugly to further fracture or endanger the integrity of the remaining bony structure. Once the IM canal 18 is prepared, the IM nail 20 may be positioned within the femur through any appropriate and generally known methods as well.

Before placing the IM nail 20 in the IM canal 18, however, an application of a bio-active material may be applied near the fracture 14 and along the IM canal 18 to assist in healing of the fracture 14 and to assist in healing of the trauma to the IM canal 18. Various bio-active materials include analgesics, antibiotics, growth factors, blood products such as platelets, and other appropriate materials. A platelet concentrate may be formed in any generally known method. Specifically, a sample of the patients blood may be taken and the platelet concentrate formed therefrom through generally known methods, such as centrifuge or filtering. It will also be understood that other sources of platelet concentrate may be used to form the platelet concentrate to be applied to the fracture 14 of the femur 10. Nevertheless, the platelet concentrate may be applied to assist in healing of the femur 10.

With reference to FIG. 2, an applicator or application system 30 is illustrated. The applicator 30 includes a supply or reservoir 32. The reservoir 32 extends along a longitudinal axis A. It will be understood, however, that the reservoir need not necessarily be straight. The supply reservoir 32 may generally include an internally moveable piston 34 associated with a piston rod 36. In this way, the reservoir 32 may be filled with the platelet concentrate and the piston 34 moved with the piston rod 36 to express the platelet concentrate from the reservoir 32 into a conduit 38.

The conduit 38 is operably connected to the reservoir 32 such that the material expressed from the reservoir 32 is directed through the conduit 38. The conduit 38 may include generally known hollow tubing which may be formed of a polymer material. The conduit 38 is able to extend into the IM canal 18 a sufficient length to reach the fracture 14. The conduit 38 includes an outlet 40. Extending from the outlet end is a nozzle 42 to direct the flow of the concentrate. The nozzle 42 may be any appropriate shape or size to selectively direct the spray S. The platelet concentrate sprayed from the nozzle 42 can be directed to any appropriate area using a control mechanism. One exemplary control mechanism includes providing the conduit 38 as a substantially stiffened tube. The tube 38 extends from the reservoir 32 and terminates in the outlet 40. The tube 38 is flexible enough to be introduced into the IM canal 18 which may not be substantially straight. Therefore, the tube 38 is able to bend around the various obstructions within the IM canal 18. However, the tube 38 is of sufficient stiffness to allow a rotational movement of the reservoir 32 to be translated to a rotation movement of a nozzle 42. Therefore, moving the reservoir 32 a selected distance moves the conduit 38 a substantially equal distance. Therefore, both rotational and translational movement of the nozzle 42 is allowed.

A second exemplary control mechanism includes supplying a selected plurality of control wires 44 and 46. The control wires 44 and 46 extend along the conduit 38 and terminate adjacent the outlet 40. In this way, the control wires 44 and 46 are operably connected with the outlet 40 and the conduit 38 such that they are used to maneuver the outlet 40 to a selected position. For example, the outlet 40 may be substantially stiffened in addition to portions of the conduit 38 such that pulling on one wire moves the nozzle 42 towards that wire and pulling on the other moves the nozzle 42 towards the other wire. In this way, the outlet 40 can be directed to a selected area to apply material to that selected area.

It will be understood, however, that various mechanisms may be used to direct the outlet 40 so that the material can be sprayed in a selected area. For example, an internal rod or mechanism can be used to direct the substantially flexible conduit 38. Nevertheless, the nozzle 42 allows the material that is expressed from the conduit 38 to be expressed in only a selected area.

During delivery of the platelet material, the nozzle 42 can be viewed using generally known external viewing devices such as fluoroscopy and x-ray viewing devices. Therefore, generally at least the outlet 40 or nozzle 42 is formed of a material that is opaque to the exterior viewing devices. For example, the nozzle 42 may be formed of a radio opaque material viewable with an x-ray apparatus. Alternatively, an indicating portion 50 may be disposed on the nozzle 42 which allows an indication of the spray S direction. As illustrated specifically in FIG. 2A, the indicating portion 50 may include a triangle which substantially defines a pointing arrow. Therefore, an x-ray or device can be used to view the direction that the material is exiting the nozzle 42. Alternatively, the entire nozzle 42 may be formed of a material which is radio opaque or can be viewed using generally known devices. It will be understood that the nozzle 42 may be a separate member which is attached to the conduit 38 such that different materials may be used and different sizes of nozzles provided for the single conduit 38 depending upon the size of the IM canal 18.

With reference to FIG. 3, an application device 60 according to various embodiments is illustrated. The application device 60 can apply a bio-active material to the IM canal 18 of a femur 10. Moreover, the material can be applied to and adjacent to the fracture 14. The application device 60 is positioned through the opening 22 formed in the distal end 12 of the femur.

The application device 60 generally includes a reservoir 62 that can be defined by a hollow body to hold a material. Positioned within the reservoir 62 is an expression system 64 to express the material from the reservoir 62. The expression system 64 includes a piston 66 and a piston rod 68. Therefore, the reservoir 62 may be filled with the material and expressed from the reservoir 62 by depressing on the expression system 64 such that the piston 66 is translated through the reservoir 62.

Formed at an end of the reservoir 62 is an outlet 70. The outlet 70 defines a nozzle 72 which can direct the material being expressed from the reservoir 62 to a selected area. Specifically, the nozzle 72 directs a spray S of the material out the nozzle 72 into a selected area. Therefore, during use, the applicator 60 is inserted into the IM canal 18 in a substantially filled state. After the nozzle 72 is positioned at a selected area, the piston 66 is pressed towards the nozzle 72 and the platelet material is expressed from the nozzle 72 to a selected area. The nozzle 72 may be formed of a substantially radio opaque material. Therefore, the direction of the spray S may be monitored by viewing the orientation of the nozzle 72. This position may be monitored using generally known external viewing devices such as x-ray, as noted above. Therefore, the nozzle 72 can be visually positioned within the IM canal 18 and adjacent to the fracture 14 before expressing the material from the applicator 60.

The spray S may be selectively repositioned by moving the reservoir 62. Because the nozzle 72 is fixed thereto, movement of the reservoir 62 is substantially directed to the nozzle 72. The applicator 60 can be rotated so that the material being expressed from the nozzle 72 can be sprayed onto a plurality of selected areas. Additionally, the applicator 60 can be moved along the length of the femur 10 to apply the material to various locations.

Figure 4:
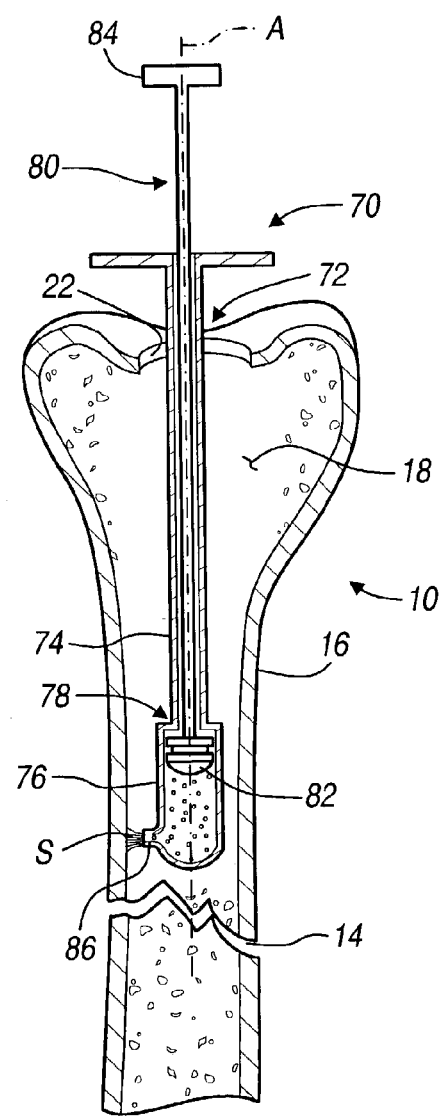
FIG. 4 is a partial cross-sectional view of a femur including an applicator according to a third embodiment.

With reference to FIG. 4, an applicator 70 to apply a material is illustrated. The applicator 70 can be positioned through the opening 22 formed in the femur 10. The applicator 70 may be positioned into the IM canal 18 of the femur 10 to apply a material. The applicator 70 includes a body 72 which includes a first or activation portion 74 and a second or reservoir portion 76. The material to be sprayed can be positioned substantially in a second portion 76. A transition area 78 is defined between the second portion 76 and the first portion 74. The size of the cross-sectional dimensions of the second portion 76 is larger than that of the first portion 74.

Moreover, the first portion 74 allows ease of maneuvering within the IM canal 18. Because the first portion 74 is smaller, it provides a larger range of motion within the IM canal. Disposed within the applicator 70 is a applicating apparatus 80 which includes a piston 82 and a piston rod 84. The piston 82 is positioned substantially within the second portion 76 while the piston rod 84 extends along the first portion 74. Therefore, the piston 82 only needs to translate along the distance of the second portion 76.

Also the piston 82 is larger than the first portion 74 and, therefore disposed substantially in the second portion 76. This also allows the material to be disposed substantially only within the second portion 76. This can reduce the amount of material that is lost within the applicator 70 and cannot be applied to the selected area. This allows for a substantially small amount of the material to be supplied within the applicator 70 to be applied to the selected area. This also allows for a small source of the material to be provided to the selected area. Nevertheless, the piston rod 84 can be depressed from outside of the femur 10.

Extending from the second portion 76 is a nozzle 86 from which a spray S of the material may occur. The nozzle 86 may be formed of a radio opaque material so that the direction of the spray S can be indicated using an external viewing device. Therefore, the direction of the nozzle 86, and therefore the position of the spray S, can be determined before the material is expressed from the applicator 70. This allows the user to determine where the material is being applied using external visualization sources.

According to various embodiments, a selected volume of material may be applied to a selected area using the applicator. Generally the material can be expressed from the applicator to the selected area through the outlet and nozzles. In this way, the material can be applied to a selected internal area and of the IM canal 18 of the femur 10. This obviates the necessity to supply the material adjacent to the bone or through soft tissue and reduces possible trauma to the soft tissue surrounding the femur. Specifically, only one incision is necessary, the same to supply the IM nail 26.

In further detail, the IM canal 18 is generally prepared to receive the IM nail 20. Before the IM nail 20 is positioned in the IM canal 18 the material can be applied within the IM canal 18 with the appropriate applicator. Therefore, the applicator is sized to fit within the prepared IM canal 18 in such that the material can be sprayed or expressed from the applicator. It will be understood that the spray is not necessarily a mist or fine spray but may include a bead or stream of material that is expressed from the applicator. Simply the material is forced from the applicator to a selected area for application of the material. Moreover, the nozzle may direct the material to more than a single direction. For example the nozzle may direct the spray to a substantial arc rather than a straight line.

After the material is applied to the selected area, the IM nail 20 is positioned into the IM canal 18. Therefore, the material is supplied to the selected area before the IM nail 20 is positioned in the IM canal 18, thereby reducing the amount of trauma that would be necessary to apply the material externally to the femur 10. Substantially only preparing the IM canal 18 for receiving the IM nail 20 is necessary to prepare the femur 10.

It will be understood that that the material applied to the IM canal is applied with the applicator. Therefore, the portion of the applicator from which the material is expressed is moved to the selected position of the bone. If the IM canal 18 is reamed then the applicator is moved into the reamed portion of the IM canal 18. Alternatively, if the IM canal 18 is not reamed then a portion of the applicator is moved through the naturally remaining portion of the IM canal 18. It will be understood, therefore, that the applicator may be positioned in the femur 10, or other appropriate bone, using the selected access method (i.e. reamed or non-reamed) for implanting the implant.

The above description is merely exemplary in nature and, thus, variations that do not depart from the gist of the description are intended to be within the scope of the following claims. Such variations are not to be regarded as a departure from the spirit and scope of the following claims. Generally, as discussed above, the above description and following claims are not limited to applying a selected material to the IM canal of a femur. It will be understood that the material may be applied to the IM canal of any selected bone. Therefore, the material can be applied to the IM canal of a humerus or tibia if a fracture occurs or IM nail is to be positioned in that bone. In addition, various other implants may be placed in various bones. For example a femoral head may include a long stem or a humeral head implant as well. Therefore, the applicator may apply a material prior to implanting these implants as well.

What is claimed is:

1. A method of applying a material to a selected area of an interior of a bone using an applicator including a nozzle to direct the flow of material from the applicator, the method comprising:

opening a portal to the interior of the bone such that a selected interior portion of the bone is exposed;

filling the applicator with the material including a platelet;

disposing the applicator in said selected interior portion of said bone; and expressing the material from the applicator having a longitudinal axis and through a tip of the applicator onto the selected interior of the bone while the applicator is disposed in the selected interior portion of the bone flexing the tip of the applicator to direct expressing the material at an angle to the longitudinal axis; and moving the tip to direct expressing the material at an angle to the longitudinal axis; and monitoring a position of a portion of the applicator.

2. The method of claim 1, wherein filling the applicator includes:

selecting the material to be expressed into the interior of the bone selected from a group comprising at least one of a growth factor, an anti-bacterial agent, an analgesic, platelet, or combinations thereof.

3. The method of claim 1, further comprising:

removing a selected volume of the interior of the bone including:

selecting an implant to be implanted in the bone;

selecting a volume appropriate for implantation of the implant; and removing the selected volume appropriate for the selected implant.

4. The method of claim 1, further comprising:

removing said applicator from said selected interior portion of the bone; and implanting a selected implant in the interior of the bone.

5. The method of claim 1, wherein:

disposing the applicator in the selected interior portion of the bone includes moving an implant through said portal;

opening a portal to the interior of the bone includes resecting a selected area of the exterior of the bone.

6. The method of claim 1, further comprising:

viewing a location of the application within the bone.

7. The method of claim 6, wherein viewing the location of the applicator includes obtaining an image of the applicator with a fluoroscope.

8. A method of applying a bio-active material to a selected interior of a bone of anatomy, the method comprising:

selecting a bone appropriate for implantation of the implant including exposing an interior surface of the selected bone;

selecting the implant for the selected bone;

preparing the selected bone appropriate for implantation of the selected implant;

disposing an applicator having a longitudinal axis and a tip within the selected bone prepared for the selected implant;

spraying the bio-active material onto the interior surface of the selected bone at least in part by flexing the tip relative to the applicator to direct spraying at an angle to the longitudinal axis; and implanting the selected implant in the selected bone.

9. The method of claim 8, wherein expressing the bio-active material into the intramedullary canal includes:

selecting a bio-active material from the group comprising at least one of an anti-bacterial agent, an analgesic, a growth factor, a platelet, and combinations thereof.

10. The method of claim 8, wherein selecting an implant to be implanted in the intramedullary canal of the selected bone including:

selecting an implant from a group comprising at least one of an intramedullary nail, femoral prosthetic, humeral prosthetic, tibial prosthetic, and combinations thereof.

11. The method of claim 8, wherein preparing the selected bone includes:

forming a portal in the selected bone; and removing a selected portion of an intramedullary canal of the selected bone.

12. The method of claim 8, wherein preparing the selected bone includes:

forming a portal to an intramedullary canal of the selected bone.

13. The method of claim 8, wherein after the spraying the bio-active material, the selected implant is positioned in the interior of the selected bone.

14. The method of claim 13 further comprising, positioning the applicator in the interior of the bone.

15. The method of claim 8, further comprising:

viewing a location of the application within the bone.

16. The method of claim 15, wherein viewing the location of the applicator includes obtaining an image of the applicator with a fluoroscope.

17. A method of applying a material to a selected area of an interior of a bone using an applicator including a nozzle to direct the flow of material from the applicator, the method comprising:

opening a portal to the interior of the bone such that a selected interior portion of the bone is exposed;

filling the applicator extending along a longitudinal axis with the material including a platelet;

disposing the applicator in said selected interior portion of said bone; and expressing the material from the applicator at an angle relative to the longitudinal axis while the applicator is disposed in the selected interior portion of the bones;

providing a tip on the applicator; and bending the tip of the applicator to direct expressing the material at an angle to the longitudinal axis.

* * * * *